(12) United States Patent
DeLuca et al.

(10) Patent No.: US 9,901,780 B2
(45) Date of Patent: Feb. 27, 2018

(54) ADJUSTING EXERCISE MACHINE SETTINGS BASED ON CURRENT WORK CONDITIONS

(71) Applicant: International Business Machines Corporation, Armonk, NY (US)

(72) Inventors: Lisa Seacat DeLuca, Baltimore, MD (US); Dana L. Price, Surf City, NC (US); Aaron J. Quirk, Cary, NC (US); Shelbee D. Smith-Eigenbrode, Thornton, CO (US)

(73) Assignee: International Business Machines Corporation, Armonk, NY (US)

( * ) Notice: Subject to any disclaimer, the term of this patent is extended or adjusted under 35 U.S.C. 154(b) by 162 days.

(21) Appl. No.: 14/844,490

(22) Filed: Sep. 3, 2015

(65) Prior Publication Data

US 2017/0065851 A1 Mar. 9, 2017

(51) Int. Cl.
*A63B 21/005* (2006.01)
*A63B 15/02* (2006.01)
(Continued)

(52) U.S. Cl.
CPC ............ *A63B 24/0087* (2013.01); *A61B 5/68* (2013.01); *A63B 22/0046* (2013.01); *A63B 22/0242* (2013.01); *G06F 19/322* (2013.01); *G06F 19/3481* (2013.01); *G06K 9/00335* (2013.01); *A63B 22/0023* (2013.01); *A63B 22/0076* (2013.01); *A63B 22/04* (2013.01); *A63B 22/0605* (2013.01); *A63B 22/0664* (2013.01); *A63B 71/0622* (2013.01); *A63B 2024/0093* (2013.01); *A63B 2071/0683* (2013.01); *A63B 2210/00* (2013.01); *A63B 2220/05* (2013.01); *A63B 2220/17* (2013.01); *A63B 2220/806* (2013.01); *A63B 2220/807* (2013.01); *A63B 2220/808* (2013.01); *A63B 2220/833* (2013.01);
(Continued)

(58) Field of Classification Search
CPC ... A63B 21/06; A63B 22/0076; A63B 22/025; A63B 22/0605; A63B 22/203; A63B 24/0062; A63B 24/0087; A63B 2024/0093
See application file for complete search history.

(56) References Cited

U.S. PATENT DOCUMENTS 5,707,319 A    1/1998 Riley
5,931,763 A *  8/1999 Alessandri ......... A63B 24/0075
                                                        482/4

(Continued)

OTHER PUBLICATIONS

Gerstacker, "Sitting Is the New Smoking: Ways a Sedentary Lifestyle Is Killing You," Huffpost Healthy Living, dated Sep. 29, 2014, 3 pages. Accessed Jun. 22, 2015, http://www.huffingtonpost.com/the-active-times/sitting-is-the-new-smokin_b_5890006.html.

(Continued)

*Primary Examiner* — Joshua Lee
(74) *Attorney, Agent, or Firm* — Yee & Associates, P.C.; John Pivnichny

(57) ABSTRACT

Adjusting settings of an exercise machine is provided. Data is received from a set of monitoring devices at a workstation. Software applications currently executing on the workstation are monitored. A signal is sent to a control module of the exercise machine adjusting one or more settings of the exercise machine based on changes in the software applications currently executing on the workstation.

16 Claims, 4 Drawing Sheets

(51) Int. Cl.
*A63B 71/00* (2006.01)
*A63B 24/00* (2006.01)
*A63B 22/02* (2006.01)
*G06F 19/00* (2018.01)
*G06K 9/00* (2006.01)
*A61B 5/00* (2006.01)
*A63B 22/00* (2006.01)
*A63B 22/06* (2006.01)
*A63B 71/06* (2006.01)
*A63B 22/04* (2006.01)

(52) U.S. Cl.
CPC ..... *A63B 2220/836* (2013.01); *A63B 2225/20* (2013.01); *A63B 2225/50* (2013.01); *A63B 2230/06* (2013.01); *A63B 2230/10* (2013.01); *A63B 2230/42* (2013.01); *A63B 2230/50* (2013.01); *A63B 2230/755* (2013.01); *G08C 2201/93* (2013.01)

(56) References Cited

U.S. PATENT DOCUMENTS

| | | | | |
|---|---|---|---|---|
| 5,984,839 | A * | 11/1999 | Corkum | A63B 71/0622 482/4 |
| 6,283,896 | B1 * | 9/2001 | Grunfeld | A63B 22/02 482/54 |
| 6,312,363 | B1 | 11/2001 | Watterson et al. | |
| 6,443,875 | B1 * | 9/2002 | Golen, Jr. | A63B 22/02 482/51 |
| 6,447,424 | B1 | 9/2002 | Ashby et al. | |
| 6,605,020 | B1 | 8/2003 | Huang | |
| 6,808,475 | B2 * | 10/2004 | Kehrbaum | A63B 22/02 482/54 |
| 6,902,513 | B1 * | 6/2005 | McClure | A63B 24/0006 482/4 |
| 7,892,148 | B1 * | 2/2011 | Stauffer | A63B 22/0235 482/51 |
| 8,965,541 | B2 | 2/2015 | Martinez et al. | |
| 8,992,383 | B2 * | 3/2015 | Bilang | A63B 22/02 482/1 |
| 2007/0265138 | A1 * | 11/2007 | Ashby | A63B 22/02 482/8 |
| 2011/0165995 | A1 | 7/2011 | Paulus et al. | |
| 2012/0040798 | A1 * | 2/2012 | Yu | A63B 22/0242 482/4 |
| 2013/0116092 | A1 * | 5/2013 | Martinez | A63B 24/0062 482/9 |
| 2015/0099952 | A1 * | 4/2015 | Lain | A61B 5/0205 600/324 |
| 2015/0196805 | A1 * | 7/2015 | Koduri | A63B 24/0087 482/6 |
| 2015/0238817 | A1 * | 8/2015 | Watterson | G06F 19/3481 482/8 |
| 2015/0360083 | A1 * | 12/2015 | Lagree | A63B 24/0075 482/130 |
| 2016/0206922 | A1 * | 7/2016 | Dalebout | A63B 24/0087 |
| 2017/0216706 | A1 * | 8/2017 | Bleich | A63B 71/0686 |

OTHER PUBLICATIONS

Yu, "The most affordable, automatic sit-to-stand desk," Kickstarter, Inc., Apr. 2, 2014, 15 pages. Accessed Jun. 22, 2015, https://www.kickstarter.com/projects/2036834894/the-most-affordable-automatic-sit-to-stand-desk.

* cited by examiner

ADJUSTING EXERCISE MACHINE SETTINGS BASED ON CURRENT WORK CONDITIONS

BACKGROUND

1. Field

The disclosure relates generally to exercise machines and more specifically to electronically adjusting settings of an active exercise machine automatically based on work conditions experienced by a user while using the exercise machine.

2. Description of the Related Art

Recent news articles have brought light on the fact that sitting for long periods of time is unhealthy. Many companies are now starting to innovate around the workspace, such as, for example, using sit to stand desks for employees to stand while working. Research shows that sitting limits a person's productivity and lowers life expectancy. Other companies are taking this notion a step further and allowing employees to multi-task their exercise through the use of treadmills underneath their workstations.

SUMMARY

According to one illustrative embodiment, a method for adjusting settings of an exercise machine is provided. A data processing system receives data from a set of monitoring devices at a workstation. The data processing system monitors software applications currently executing on the workstation. The data processing system sends a signal to a control module of the exercise machine adjusting one or more settings of the exercise machine based on changes in the software applications currently executing on the workstation. According to other illustrative embodiments, a data processing system and computer program product for adjusting settings of an exercise machine are provided.

DETAILED DESCRIPTION

Figure 1:
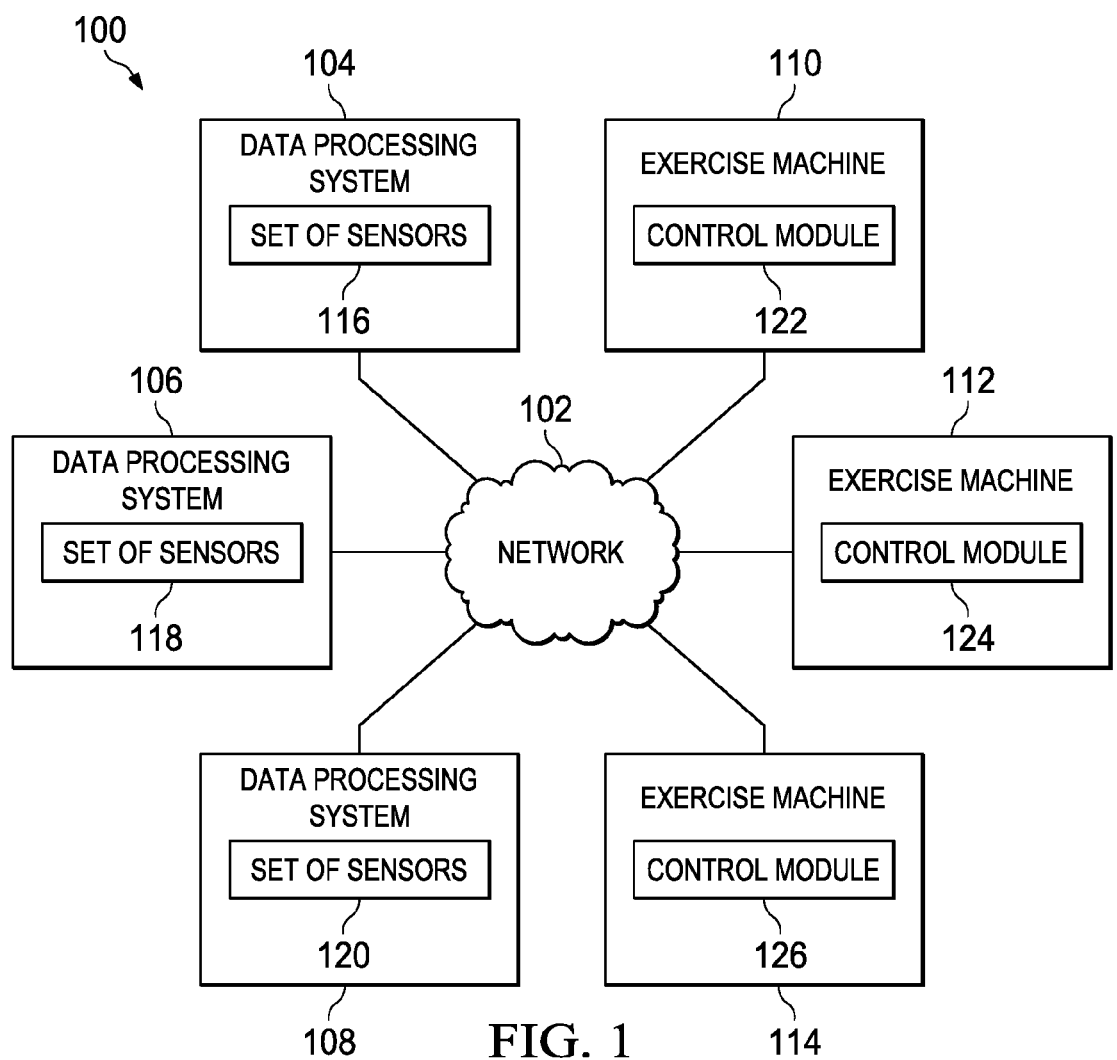
FIG. 1 is a pictorial representation of a network of data processing systems in which illustrative embodiments may be implemented.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer readable program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
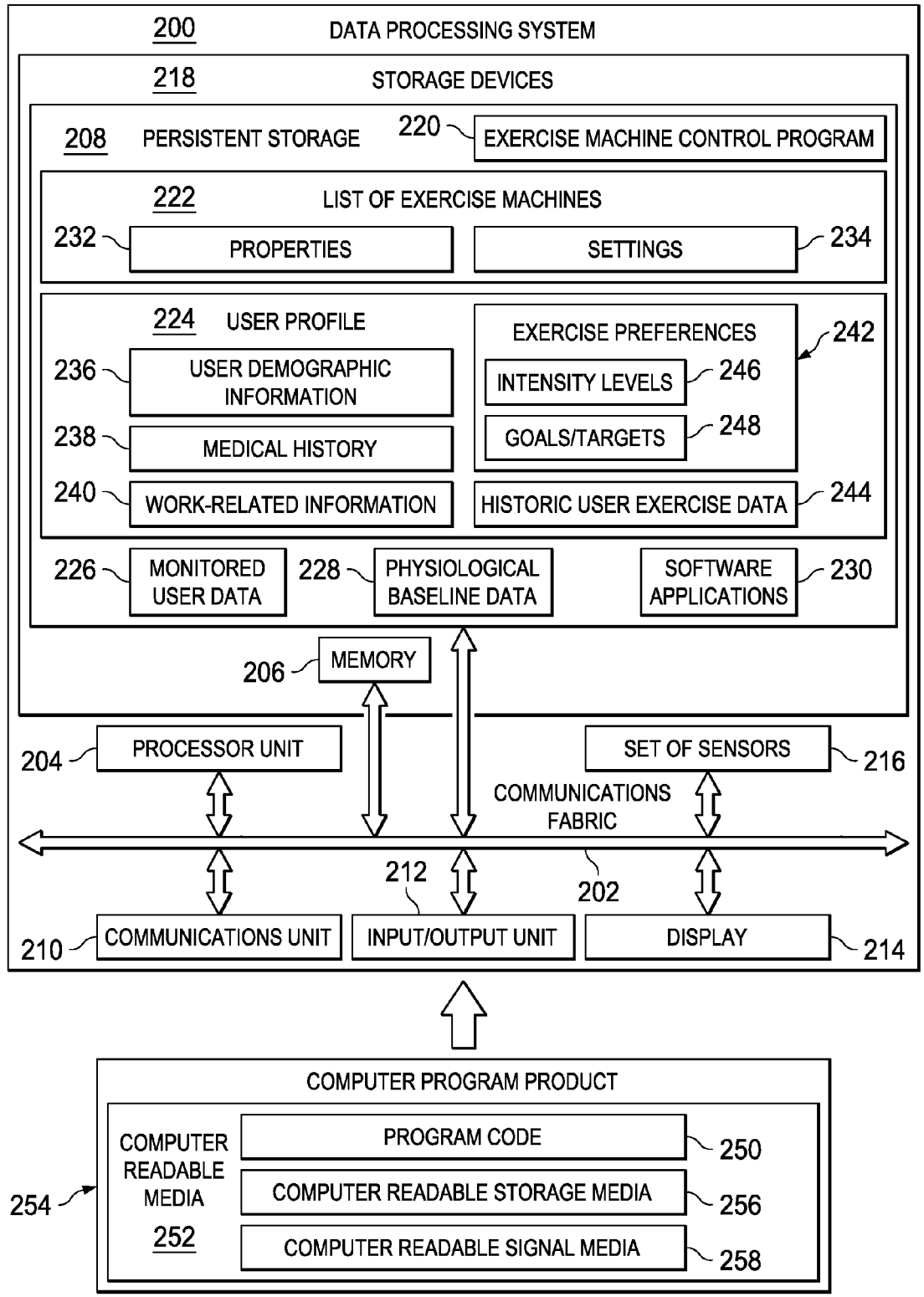
FIG. 2 is a diagram of a data processing system in which illustrative embodiments may be implemented.
Figure 3:
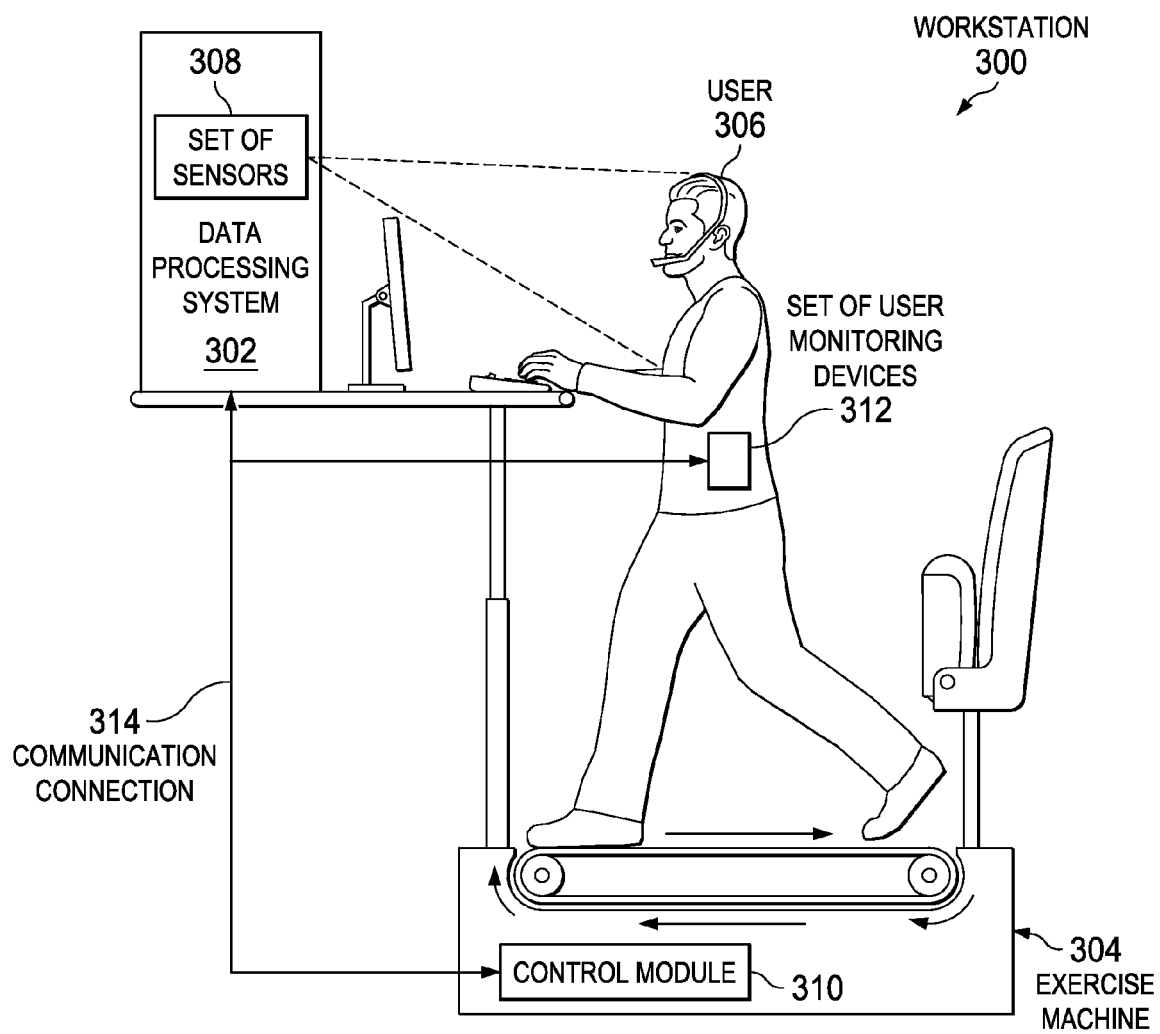
FIG. 3 is a diagram of an example of a workstation in accordance with an illustrative embodiment.

With reference now to the figures, and in particular, with reference to FIGS. 1-3, diagrams of data processing environments are provided in which illustrative embodiments may be implemented. It should be appreciated that FIGS. 1-3 are only meant as examples and are not intended to assert or imply any limitation with regard to the environments in which different embodiments may be implemented. Many modifications to the depicted environments may be made.

FIG. 1 depicts a pictorial representation of a network of data processing systems in which illustrative embodiments may be implemented. Network data processing system 100 is a network of data processing systems, exercise machines, and other devices in which the illustrative embodiments may be implemented. Network data processing system 100 contains network 102, which is the medium used to provide communications links between the data processing systems, exercise machines, and the other devices connected together within network data processing system 100. Network 102 may include connections, such as, for example, wireless communication links, wire communication links, and fiber optic cables.

In the depicted example, data processing system 104, data processing system 106, and data processing system 108 connect to network 102. Data processing system 104, data processing system 106, and data processing system 108 may be, for example, network computers, desktop computers, laptop computers, tablet computers, wearable data processing systems, such as smart watches, smart phones, personal digital assistants, gaming devices, landline telephones, or any combination thereof. Exercise machine 110, exercise machine 112, and exercise machine 114 also connect to network 102. Exercise machine 110, exercise machine 112, and exercise machine 114 may be, for example, treadmill machines, stair climber machines, elliptical machines, bicycle machines, skiing machines, rowing machines, weight machines, resistance training machines, or any combination thereof.

In this example, data processing system 104, data processing system 106, and data processing system 108 include set of sensors 116, set of sensors 118, and set of sensors 120, respectively. Set of sensors 116, set of sensors 118, and set of sensors 120 may include, for example, one or more imaging devices, such as still picture cameras, video cameras, and infrared cameras, and one or more sound detection devices, such as microphones. Data processing system 104, data processing system 106, and data processing system 108 may utilize set of sensors 116, set of sensors 118, and set of sensors 120 to collect data corresponding to users of exercise machine 110, exercise machine 112, and exercise machine 114. For example, set of sensors 116, set of sensors 118, and set of sensors 120 may monitor facial expressions, pupil dilation, skin flushing, speech patterns, tone of speech, language used in speech, utterances, sounds, and the like. Further, set of sensors 116, set of sensors 118, and set of sensors 120 may monitor users of data processing system 104, data processing system 106, and data processing system 108 to determine how the users are interacting with data processing system 104, data processing system 106, and data processing system 108, such as keyboarding speed, input error rate, number of open software applications, and the like.

In this example, data processing system 104, data processing system 106, and data processing system 108 monitor users of exercise machine 110, exercise machine 112, and exercise machine 114, respectively. In addition, data processing system 104, data processing system 106, and data processing system 108 are capable of automatically adjusting the settings of exercise machine 110, exercise machine 112, and exercise machine 114, respectively, based on data received from set of sensors 116, set of sensors 118, and set of sensors 120 and other stored or received information. The settings may include, for example, time (i.e., duration), speed, inclination, interval, resistance, direction of movement, and the like.

For example, data processing system 104, data processing system 106, and data processing system 108 may automatically increase the time, speed, inclination, interval, and resistance settings of exercise machine 110, exercise machine 112, and exercise machine 114 by sending an electronic signal to control module 122, control module 124, and control module 126 to make the appropriate adjustments on a corresponding exercise machine. Similarly, data processing system 104, data processing system 106, and data processing system 108 may automatically decrease the time, speed, inclination, interval, and resistance settings of exercise machine 110, exercise machine 112, and exercise machine 114. In addition, data processing system 104, data processing system 106, and data processing system 108 may automatically increase some settings while decreasing other settings of exercise machine 110, exercise machine 112, and exercise machine 114. Moreover, data processing system 104, data processing system 106, and data processing system 108 may automatically reverse direction of movement of exercise machine 110, exercise machine 112, and exercise machine 114.

Further, it should be noted that one data processing system may monitor and control the settings of two or more different types of exercise machines. Furthermore, a set of one or more exercise machines may be located at a workstation of a user who is utilizing the set of exercise machines while performing work-related activities. Moreover, data processing system 104, data processing system 106, and data processing system 108 may provide software programs to exercise machine 110, exercise machine 112, and exercise machine 114.

In addition, it should be noted that network data processing system 100 may include any number of additional data processing systems, exercise machines, networks, and other devices, such as storage devices, not shown. Program code located in network data processing system 100 may be stored on a storage medium and downloaded to a data processing system or exercise machine for use. For example, program code may be stored on a storage medium on data processing system 104 and downloaded to exercise machine 110 over network 102 for use on exercise machine 110.

In the depicted example, network data processing system 100 may be implemented as a number of different types of communication networks, such as, for example, an intranet, a local area network (LAN), a personal area network (PAN), an internet, and a wide area network (WAN). FIG. 1 is intended as an example, and not as an architectural limitation for the different illustrative embodiments.

With reference now to FIG. 2, a diagram of a data processing system is depicted in accordance with an illustrative embodiment. Data processing system 200 may be, for example, data processing system 104 in FIG. 1, in which program instructions implementing processes of illustrative embodiments may be located. In this illustrative example, data processing system 200 includes communications fabric 202, which provides communications between processor unit 204, memory 206, persistent storage 208, communications unit 210, input/output (I/O) unit 212, display 214, and set of sensors 216.

Processor unit 204 serves to execute instructions for software applications and programs that may be loaded into memory 206. Processor unit 204 may be a set of one or more hardware processor devices or may be a multi-processor core, depending on the particular implementation. Further, processor unit 204 may be implemented using one or more heterogeneous processor systems, in which a main processor is present with secondary processors on a single chip. As another illustrative example, processor unit 204 may be a symmetric multi-processor system containing multiple processors of the same type.

Memory 206 and persistent storage 208 are examples of storage devices 218. A storage device is any piece of hardware that is capable of storing information, such as, for example, without limitation, data, program instructions in functional form, and/or other suitable information either on a transient basis and/or a persistent basis. Further, a storage device excludes a propagation medium. Memory 206, in these examples, may be, for example, a random access memory, or any other suitable volatile or non-volatile storage device. Persistent storage 208 may take various forms, depending on the particular implementation. For example, persistent storage 208 may contain one or more devices. For example, persistent storage 208 may be a hard drive, a flash memory, a rewritable optical disk, a rewritable magnetic tape, or some combination of the above. The media used by persistent storage 208 may be removable. For example, a removable hard drive may be used for persistent storage 208.

In this example, persistent storage 208 stores exercise machine control program 220, list of exercise machines 222, user profile 224, monitored user data 226, physiological baseline data 228, and software applications 230. Data processing system 200 utilizes exercise machine control program 220 to automatically adjust or modify one or more settings of an exercise machine, such as, exercise machine 110 in FIG. 1. List of exercise machines 222 is a list of one or more exercise machines that exercise machine control program 220 is able to control remotely. List of exercise machines 222 includes properties 232 and settings 234. Properties 232 include types of exercise machines and related specification information. Settings 234 include the different types of settings corresponding to each exercise machine listed.

In this example, user profile 224 includes user demographic information 236, medical history 238, work-related information 240, exercise preferences 242, and historic user exercise data 244. However, different illustrative embodiments may include more or less data in user profile 224. User demographic information 236 may include, for example, the age, gender, occupation, and employer of a user corresponding to data processing system 200. Medical history 238 may be input by the user of data processing system 200 and may include general health information regarding the user, such as heart health, serious diseases, and serious injuries. Medical history 238 also may include medical records from doctors' offices and/or hospitals, which data processing system 200 may retrieve from remote databases containing such records via a network, such as network 102 in FIG. 1.

Work-related information 240 may include, for example, current job duties performed by the user, work schedule, such as days and hours worked, names of managers and co-workers, and the like. Exercise preferences 242 include intensity levels 246 and goals/targets 248. Intensity levels 246 may include, for example, different levels of exercise intensity the user likes to exercise at and when the user likes to exercise. Goals/targets 248 may include, for example, daily, weekly, and monthly user-defined exercise goals or targets. Historic user exercise data 244 may include, for example, a record of exercise machines previously used by the user, workout schedules, workout durations, intensity levels, exercise machine settings, and the like.

Monitored user data 226 is incoming real time data corresponding to the user while the user is exercising at a workstation. Monitored user data 226 may be received from set of sensors 216 and/or from a set of user monitoring devices located on the user.

Physiological baseline data 228 may be generic baseline physiological baseline data relating to humans in general, which data processing system 200 may have retrieved from remote databases storing such information. Alternatively, physiological baseline data 228 may be specific to the user of data processing system 200. For example, the user of data processing system 200 may have previously trained the set of user monitoring devices, which are worn by the user, to collect baseline readings on the user prior to starting an exercise program on an exercise machine at the workstation. Data processing system 200 may utilize physiological baseline data 228 to compare with incoming real time monitored user data 226 corresponding to the user while the user is exercising at the workstation to determine appropriate adjustments to the settings of the exercise machine.

Software applications 230 is a list of software applications currently active within data processing system 200 and may include information regarding activities within each of the software applications by the user. Software applications 230 may include, for example, telephone applications, teleconferencing applications, texting applications, email applications, calendar applications, word processing applications, and any other type of work-related application. Data processing system 200 may utilize information in software applications 230 to determine appropriate adjustments to the settings of the exercise machine.

Communications unit 210, in this example, provides for communication with other data processing systems, exercise machines, and devices via a network, such as network 102 in FIG. 1. Communications unit 210 may provide communications through the use of both physical and wireless communications links. The physical communications link may utilize, for example, a wire, cable, universal serial bus, or any other physical technology to establish a physical communications link for data processing system 200. The wireless communications link may utilize, for example, shortwave, high frequency, ultra high frequency, microwave, wireless fidelity (Wi-Fi), bluetooth technology, global system for mobile communications (GSM), code division multiple access (CDMA), second-generation (2G), third-generation (3G), fourth-generation (4G), 4G Long Term Evolution (LTE), LTE Advanced, or any other wireless communication technology or standard to establish a wireless communications link for data processing system 200.

Input/output unit 212 allows for the input and output of data with other devices that may be connected to data processing system 200. For example, input/output unit 212 may provide a connection for user input through a keypad, a keyboard, a mouse, and/or some other suitable input device. Display 214 provides a mechanism to display information to a user and may include touch screen capabilities to allow the user to make on-screen selections through user interfaces or input data, for example.

Set of sensors 216 may be, for example, set of sensors 116 in FIG. 1. Set of sensors 216 may include, for example, a set of one or more imaging devices and a set of one or more sound detection devices. Data processing system 200 may utilize set of sensors 216 to monitor the user of data processing system 200 while the user is exercising on the exercise machine at the workstation to determine appropriate adjustments to the settings of the exercise machine.

Instructions for the operating system, applications, and/or programs may be located in storage devices 218, which are in communication with processor unit 204 through communications fabric 202. In this illustrative example, the instructions are in a functional form on persistent storage 208. These instructions may be loaded into memory 206 for running by processor unit 204. The processes of the different embodiments may be performed by processor unit 204 using program instructions, which may be located in a memory, such as memory 206. These program instructions are referred to as program code that may be read and run by a processor in processor unit 204. The program code, in the different embodiments, may be embodied on different physical computer readable storage devices, such as memory 206 or persistent storage 208.

Program code 250 is located in a functional form on computer readable media 252 that is selectively removable and may be loaded onto or transferred to data processing system 200 for running by processor unit 204. Program code 250 and computer readable media 252 form computer program product 254. In one example, computer readable media 252 may be computer readable storage media 256 or computer readable signal media 258. Computer readable storage media 256 may include, for example, an optical or magnetic disc that is inserted or placed into a drive or other device that is part of persistent storage 208 for transfer onto a storage device, such as a hard drive, that is part of persistent storage 208. Computer readable storage media 256 also may take the form of a persistent storage, such as a hard drive, a thumb drive, or a flash memory that is connected to data processing system 200. In some instances, computer readable storage media 256 may not be removable from data processing system 200.

Alternatively, program code 250 may be transferred to data processing system 200 using computer readable signal media 258. Computer readable signal media 258 may be, for example, a propagated data signal containing program code 250. For example, computer readable signal media 258 may be an electro-magnetic signal, an optical signal, and/or any other suitable type of signal. These signals may be transmitted over communication links, such as wireless communication links, an optical fiber cable, a coaxial cable, a wire, and/or any other suitable type of communications link. In other words, the communications link and/or the connection may be physical or wireless in the illustrative examples. The computer readable media also may take the form of non-tangible media, such as communication links or wireless transmissions containing the program code.

In some illustrative embodiments, program code 250 may be downloaded over a network to persistent storage 208 from another device or data processing system through computer readable signal media 258 for use within data processing system 200. For instance, program code stored in a computer readable storage media in a data processing system may be downloaded over a network from the data processing system to data processing system 200. The data processing system providing program code 250 may be a server computer, a client computer, or some other device capable of storing and transmitting program code 250.

The different components illustrated for data processing system 200 are not meant to provide architectural limitations to the manner in which different embodiments may be implemented. The different illustrative embodiments may be implemented in a data processing system including components in addition to, or in place of, those illustrated for data processing system 200. Other components shown in FIG. 2 can be varied from the illustrative examples shown. The different embodiments may be implemented using any hardware device or system capable of executing program code. As one example, data processing system 200 may include organic components integrated with inorganic components and/or may be comprised entirely of organic components excluding a human being. For example, a storage device may be comprised of an organic semiconductor.

As another example, a computer readable storage device in data processing system 200 is any hardware apparatus that may store data. Memory 206, persistent storage 208, and computer readable storage media 256 are examples of physical storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

In the course of developing illustrative embodiments, it was discovered that a user manually adjusts the settings of an exercise machine. One problem with manually adjusting the settings is that the user will not get the most out of a workout by taking advantage of listening to the user's body and determining working conditions to be as productive as possible. Illustrative embodiments automatically adjust an active exercise machine, such as a treadmill, based on working conditions of the user at a workstation. Thus, illustrative embodiments may provide maximum physical benefit to the user while allowing the user to be productive at work-related tasks.

Illustrative embodiments connect an exercise machine's control module to one or more data processing systems corresponding to the user, such as, for example, a desktop computer, a laptop computer, mobile telephone phone, a tablet computer, a wearable data processing system, such as a smart watch, a landline phone, a gaming device, and the like. Illustrative embodiments establish the connection between the exercise machine's control module and the one or more user data processing systems using standard connection protocols, such as, for example, a bluetooth technology connection, a wireless fidelity (WiFi) connection, a direct wire connection, and the like.

Illustrative embodiments may automatically adjust settings of the exercise machine's control module based on received sensor data. The settings of the exercise machine's control module may include, for example, time duration, speed, incline, decline, interval, resistance, direction (i.e., forward or backward direction), target heart rate of the user, and the like. Illustrative embodiments may adjust the settings of the exercise machine's control module to increase exercise intensity in response to certain user exercise preferences, such as, for example: 1) identification of a particular work-related activity being performed by the user (e.g., increase exercise intensity when doing an activity that might be considered leisurely, such as reading work emails); 2) identification of a particular phone usage by the user (e.g., increase exercise intensity when the user is listening, while on mute, to a conference call); 3) identification of a particular emotions being experienced by the user (e.g., increase exercise intensity to increase endorphin levels of the user to increase a feeling of well-being in the user when the user gets angry at a coworker over content of an instant message); 4) identification of a particular person who the user is currently interacting with (e.g., increase exercise intensity when talking with co-worker Bob who is excited about a new project); 5) identification of a particular calendared event (e.g., increase exercise intensity when on a teleconference with greater than five other co-workers, as the user is likely not to be talking); and 6) identification of a particular level of daily physical activity of the user (e.g., increase exercise intensity to a higher level during "slower" work periods when the user has not yet reached the user's daily goals for physical activity).

Similarly, illustrative embodiments may adjust the settings of the exercise machine's control module to decrease exercise intensity in response to certain user exercise preferences, such as, for example: 1) identification of a particular work-related activity being performed by the user (e.g., decrease exercise intensity when the user is performing an activity requiring more concentration, such as when using a drawing program or when typing rapidly and making more mistakes than usual, which illustrative embodiments may identify by the user using the backspace key more than usual); 2) identification of a particular phone usage by the user (e.g., decrease exercise intensity when the user takes the telephone off mute and is actively speaking during a conference call); 3) identification of a particular teleconference conversation context (e.g., decrease exercise intensity when the user's name or a name of a project the user is working on is mentioned during the teleconference so the user can focus on what is being said); 4) identification of a particular emotion being experienced by the user (e.g., decrease exercise intensity when the user utilizes certain keywords, such as "sad" or "upset", while texting or posting content on a social media website); 5) identification of a particular person who the user is currently interacting with (e.g., decrease exercise intensity when talking with manager Mary because the user doesn't want Mary to hear the exercise machine in the background or the user doesn't want to sound out of breath, or decrease exercise intensity when talking with customer Eric because Eric has a speaking cadence or a foreign accent that requires additional concentration by the user to understand what Eric is saying); 6) identification of a particular calendared events (e.g., decrease exercise intensity when the user is on a teleconference with three people or less as the user is likely to be talking and shouldn't sound out of breath, decrease exercise intensity when the user is listed as the teleconference host or chair, or decrease exercise intensity when the user is on a teleconference with recognized customer contacts); and 7) identification of a particular level of daily physical activity of user (e.g., decrease exercise intensity to a lower level or stop the exercise machine when the user has reached the user's daily goals for physical activity or to give the user a break period).

As illustrative embodiments receive data, illustrative embodiments continue to determine whether to adjust settings of the exercise machine's control module. In addition, illustrative embodiments may utilize historical user exercise analytics to determine how the user performs when talking to certain individuals. For example, the user may burn more calories when talking to manager Bob then when the user talks to co-worker Joe. Further, illustrative embodiments may have previously recorded which exercise machine settings had the most impact on biometric output of the user and use that information to currently adjust the settings based on those biometrics. For example, illustrative embodiments don't just automatically decrease exercise machine intensity levels, but recognize the pattern of changes that are most effective in reducing the user's physical exertion. As a specific example, the user may struggle most with an exercise machine decline due to a previous knee injury, but illustrative embodiments may have determined that the user is still able to handle a brisk pace. Thus, illustrative embodiments may analyze different exercise machine settings and user exertion patterns to develop a custom exertion pattern for the user to apply across user exercise preferences. Further, illustrative embodiments over a period of time may determine the time of day when the user is most efficient at calorie burning (or other biometric measure) and use that information to assist the user in reaching goals or targets by increasing intensity a little more than usual in those times of increased calorie burning.

With reference now to FIG. 3, a diagram of an example of a workstation is depicted in accordance with an illustrative embodiment. Workstation 300 may be implemented in a network of data processing systems, such as network data processing system 100 in FIG. 1. In this example, workstation 300 includes data processing system 302 and exercise machine 304. However, it should be noted that workstation 300 may include other components, such as, for example, an adjustable desk top and seat. Further, it should be noted that even though this example illustrates that exercise machine 304 is integrated into workstation 300, alternative illustrative embodiments may have exercise machine as a separate component that may be located under or near the adjustable desk top or work surface.

Workstation 300 is where user 306 performs work-related activities. In addition, workstation 300 allows user 306 to exercise on exercise machine 304 while performing the work-related activities. Data processing system 302 may be, for example, data processing system 104 in FIG. 1 and data processing system 200 in FIG. 2. In this example, data processing system 302 includes set of sensors 308, such as, set of sensors 116 in FIG. 1 or set of sensors 216 in FIG. 2. Data processing system 302 controls the functioning of exercise machine 304 by automatically adjusting settings of control module 310 in exercise machine 304 based on data received from at least one of set of sensors 308 and set of user monitoring devices 312.

For example, data processing system 302 may send an electronic signal via communication connection 314 to control module 310 adjusting the settings of exercise machine 304 based on data corresponding to user 306, which is received from at least one of set of sensors 308 and set of user monitoring devices 312, while user 306 is exercising on exercise machine 304 and performing work-related activities. Exercise machine 304 is capable of providing a variety of different exercise intensity levels through adjustments to settings, such as, for example, increasing and decreasing speed, duration, inclination, resistance, or any combination thereof. Set of sensors 308 may be, for example, imaging and sound detection devices to monitor user 306 for facial expressions and sounds. Set of sensors 308 also may include sensors for determining how a user of data processing system 302 is interacting with data processing system 302, such as number of keystrokes per minute, number of backspacing per minute, number of open applications, number of times applications are opened and closed, et cetera.

Set of user monitoring devices 312 are located on or worn by user 306 in various places on the body of user 306. Set of user monitoring devices 312 may monitor user 306 for indications as to user 306's current cognitive and physical state. For example, set of user monitoring devices 312 may monitor user 306 for rapid eye movements, which may indicate distraction, pupil dilation, which may indicate fear or stress, degree to which the eyes are closed, which may indicate drowsiness, and the like. Set of user monitoring devices 312 may be a set of one or more monitoring devices that may include an eye tracking monitor, heart rate monitor, respiration rate monitor, temperature monitor, and/or skin monitor that are capable of monitoring the user for measurable physiological changes in user 306 indicating current cognitive and physical state of user 306. Set of user monitoring devices 312 also may include a portable brain-wave monitor, such as, for example, a portable electroencephalogram (EEG) machine, which may measure and record changes in electrical activity of a brain over a period of time indicating the current cognitive state of user 306. In other words, set of user monitoring devices 312 may monitor user 306 for any type of physiological changes, such as, for example, neurophysiological, electrophysiological, and cognitive psychophysiological changes in user 306.

Set of user monitoring devices 312 generate monitored user data, such as, for example, monitored user data 226 in FIG. 2. Set of user monitoring devices 312 are coupled to data processing system 302 via wireless and/or wire communication links. Set of user monitoring devices 312 transmit the monitored user data to data processing system 302 on a real time or near real time basis. Data processing system 302 may utilize the monitored user data to automatically adjust the setting of exercise machine 304 based on the current cognitive and physical state of user 306. User 306 may have previously trained set of user monitoring devices 312 to collect baseline readings on user 306.

Figure 4:
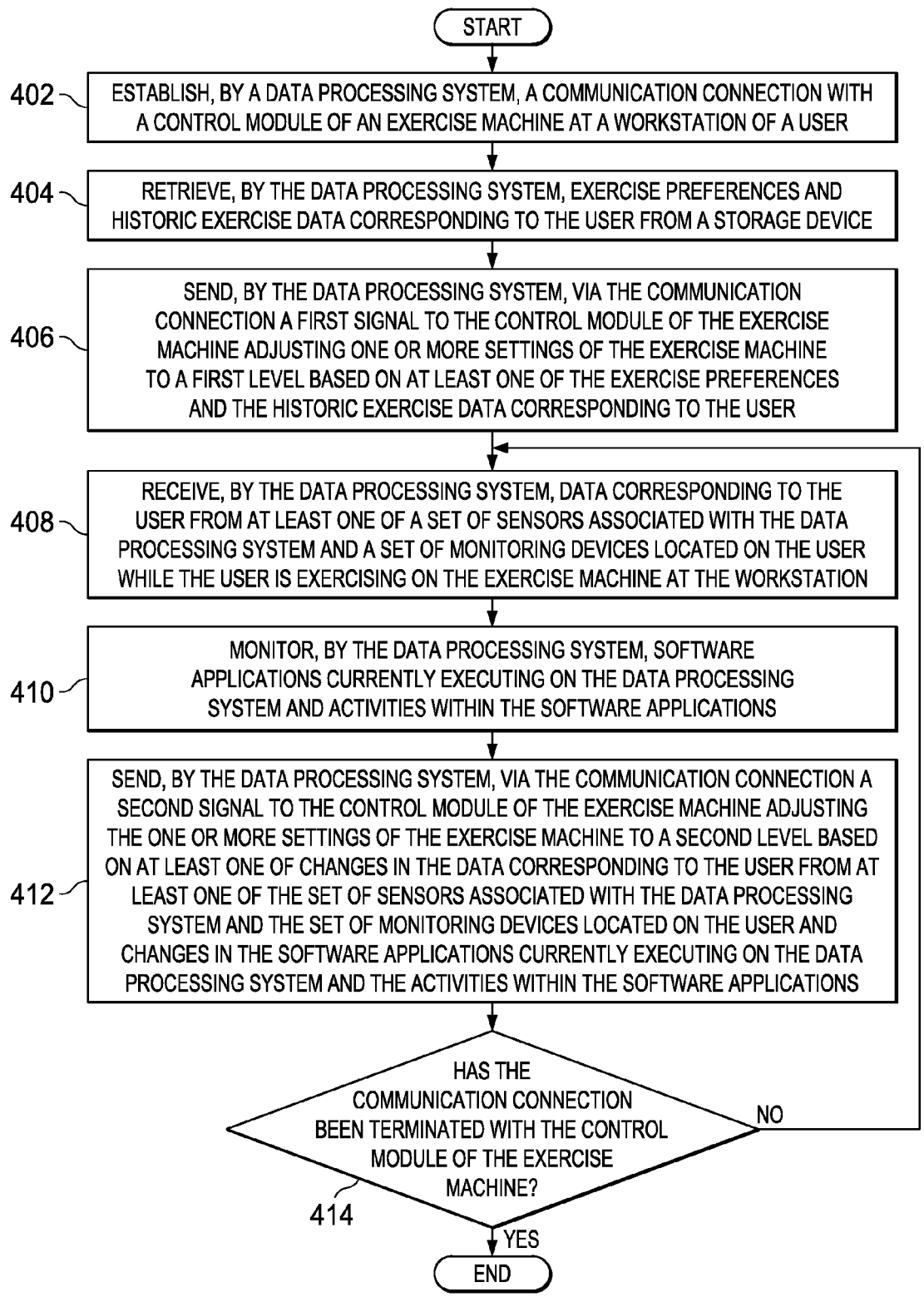
FIG. 4 is a flowchart illustrating a process for adjusting settings of an exercise machine in accordance with an illustrative embodiment.

With reference now to FIG. 4, a flowchart illustrating a process for adjusting settings of an exercise machine is shown in accordance with an illustrative embodiment. The process shown in FIG. 4 may be implemented in a data processing system, such as, for example, data processing system 104 in FIG. 1, data processing system 200 in FIG. 2, or data processing system 302 in FIG. 3.

The process begins when the data processing system establishes a communication connection with a control module of an exercise machine at a workstation of a user (step 402). The communication connection may be, for example, communication connection 314 between data processing system 302 and control module 310 of exercise machine 304 in FIG. 3. In addition, the communication connection may be, for example, a bluetooth technology connection. The workstation and user may be, for example, workstation 300 and user 306 in FIG. 3.

The data processing system also retrieves exercise preferences and historic exercise data corresponding to the user from a storage device (step 404). The exercise preferences and historic exercise data may be, for example, exercise preferences 242 and historic user exercise data 244 stored in persistent storage 208 in FIG. 2. Afterward, the data processing system sends, via the communication connection, a first signal to the control module of the exercise machine adjusting one or more settings of the exercise machine to a first level based on at least one of the exercise preferences and the historic exercise data corresponding to the user (step 406).

Subsequently, the data processing system receives data corresponding to the user from at least one of a set of sensors associated with the data processing system and a set of monitoring devices located on the user while the user is exercising on the exercise machine at the workstation (step 408). The set of sensors associated with the data processing system and the set of monitoring devices located on the user may be, for example, set of sensors 308 and set of user monitoring devices 312 in FIG. 3. In addition, the data processing system monitors software applications currently executing on the data processing system and activities within the software applications (step 410). The software applications may be, for example, software applications 230 in FIG. 2.

Further, the data processing system sends, via the communication connection, a second signal to the control module of the exercise machine adjusting the one or more settings of the exercise machine to a second level based on at least one of changes in the data corresponding to the user from at least one of the set of sensors associated with the data processing system and the set of monitoring devices located on the user and changes in the software applications currently executing on the data processing system and the activities within the software applications (step 412). Furthermore, the data processing system makes a determination as to whether the communication connection has been terminated with the control module of the exercise machine (step 414). If the data processing system determines that the communication connection has not been terminated with the control module of the exercise machine, no output of step 414, then the process returns to step 408 where the data processing system continues to receive data corresponding to the user. If the data processing system determines that the communication connection has been terminated with the control module of the exercise machine, yes output of step 414, then the process terminates thereafter.

Thus, illustrative embodiments provide a method, data processing system, and computer program product for adjusting settings of an active exercise machine automatically based on work conditions experienced by a user while using the exercise machine. The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiment. The terminology used herein was chosen to best explain the principles of the embodiment, the practical application or technical improvement over technologies found in the marketplace, or to enable others of ordinary skill in the art to understand the embodiments disclosed here.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method for adjusting settings of an exercise machine, the method comprising:
   receiving, by a data processing system, data from a set of sensors of the data processing system, wherein the data processing system is coupled to the exercise machine at a workstation corresponding to a user who is utilizing the exercise machine while performing activities on the data processing system;
   monitoring, by the data processing system, the activities performed by the user in software applications currently executing on the data processing system at the workstation using the data from the set of sensors, wherein the set of sensors includes one or more imaging devices and one or more sound detection devices that monitor facial expressions, pupil dilation, skin flushing, speech patterns, tone of speech, language used in speech, utterances, and sounds of the user while the user is exercising on the exercise machine and performing the activities in the software applications currently executing on the data processing system, and wherein the set of sensors also includes sensors for determining how the user is interacting with the data processing system by monitoring a number of keystrokes per minute and a number of backspacing per minute by the user while performing the activities in the software applications currently executing on the data processing system;
   sending, by the data processing system, a signal to a control module of the exercise machine adjusting one or more settings of the exercise machine based on changes in the activities the user is performing in the software applications currently executing on the data processing system at the workstation; and
   adjusting, by the data processing system, the one or more settings of the exercise machine based on a current cognitive state of the user determined by a portable brain-wave monitor coupled to the data processing system that monitors the user for measurable cognitive psychophysiological changes indicating the current cognitive state of the user.

2. The method of claim 1 further comprising:
   retrieving, by the data processing system, work-related information that includes current job duties corresponding to the user from a storage device.

3. The method of claim 2 further comprising:
   adjusting, by the data processing system, the one or more settings of the exercise machine based on the work-related information corresponding to the user.

4. The method of claim 1, wherein the adjusting of the one or more settings of the exercise machine includes at least one of changing a time duration setting, a speed setting, an inclination setting, an interval setting, a resistance setting, and a direction of movement setting.

5. The method of claim 1 further comprising:
   adjusting, by the data processing system, the one or more settings of the exercise machine to increase exercise intensity based on exercise preferences of the user, wherein exercise preferences of the user are at least one of increase exercise intensity when the user is reading work-related emails, increase exercise intensity when the user is on mute during a telephone call, increase exercise intensity when the user gets angry, increase exercise intensity when the user is talking with an excited co-worker, increase exercise intensity when the user is on a teleconference with greater than five other co-workers, and increase exercise intensity during slower work periods when the user has not yet reached daily goals for physical activity.

6. The method of claim 1 further comprising:
   adjusting, by the data processing system, the one or more settings of the exercise machine to decrease exercise intensity based on exercise preferences of the user, wherein the exercise preferences of the user are at least one of decrease exercise intensity when the user is performing an activity requiring increased concentration, decrease exercise intensity when the user takes a telephone off mute and is actively speaking, decrease exercise intensity when one of a name of the user or a name of a project the user is working on is mentioned during a telephone call, decrease exercise intensity when the user utilizes certain keywords while inputting text, decrease exercise intensity when the user is talking with one of a manager or a customer, decrease exercise intensity when the user is on a teleconference with three people or less, decrease exercise intensity when the user is listed as a host of the teleconference, decrease exercise intensity when the user has reached daily goals for physical activity.

7. The method of claim 1, wherein the exercise machine is one of a treadmill machine, a stair climber machine, an elliptical machine, a bicycle machine, a skiing machine, a rowing machine, a weight machine, or a resistance training machine.

8. The method of claim 1, wherein the data processing system is one of a network computer, a desktop computer, a laptop computer, a tablet computer, a wearable data processing system, a smart phone, a personal digital assistant, a gaming device, or a landline telephone.

9. The method of claim 1 further comprising:
monitoring, by the data processing system, how the user is interacting with the data processing system while the user is performing the activities in the software applications currently executing on the data processing system and exercising on the exercise machine at the workstation; and
adjusting, by the data processing system, the one or more settings of the exercise machine based on how the user is interacting with the data processing system while the user is performing the activities in the software applications currently executing on the data processing system.

10. A data processing system for adjusting settings of an exercise machine, the data processing system comprising:
a bus system;
a storage device connected to the bus system, wherein the storage device stores program instructions; and
a processor connected to the bus system, wherein the processor executes the program instructions to:
receive data from a set of sensors of the data processing system, wherein the data processing system is coupled to the exercise machine at a workstation corresponding to a user who is utilizing the exercise machine while performing activities on the data processing system;
monitor the activities performed by the user in software applications currently executing on the data processing system at the workstation using the data from the set of sensors, wherein the set of sensors includes one or more imaging devices and one or more sound detection devices that monitor facial expressions, pupil dilation, skin flushing, speech patterns, tone of speech, language used in speech, utterances, and sounds of the user while the user is exercising on the exercise machine and performing the activities in the software applications currently executing on the data processing system, and wherein the set of sensors also includes sensors for determining how the user is interacting with the data processing system by monitoring a number of keystrokes per minute and a number of backspacing per minute by the user while performing the activities in the software applications currently executing on the data processing system;
send a signal to a control module of the exercise machine adjusting one or more settings of the exercise machine based on changes in the activities the user is performing in the software applications currently executing on the data processing system at the workstation; and
adjust the one or more settings of the exercise machine based on a current cognitive state of the user determined by a portable brain-wave monitor coupled to the data processing system that monitors the user for measurable cognitive psychophysiological changes indicating the current cognitive state of the user.

11. The data processing system of claim 10, wherein the processor further executes the program instructions to:
retrieve work-related information that includes current job duties corresponding to the user from the storage device.

12. The data processing system of claim 11, wherein the processor further executes the program instructions to:
adjust the one or more settings of the exercise machine based on the work-related information corresponding to the user.

13. A computer program product for adjusting settings of an exercise machine, the computer program product comprising a computer readable storage medium having program instructions embodied therewith, the program instructions executable by a data processing system to cause the data processing system to perform a method comprising:
receiving, by the data processing system, data from a set of sensors of the data processing system, wherein the data processing system is coupled to the exercise machine at a workstation corresponding to a user who is utilizing the exercise machine while performing activities on the data processing system;
monitoring, by the data processing system, the activities performed by the user in software applications currently executing on the data processing system at the workstation using the data from the set of sensors, wherein the set of sensors includes one or more imaging devices and one or more sound detection devices that monitor facial expressions, pupil dilation, skin flushing, speech patterns, tone of speech, language used in speech, utterances, and sounds of the user while the user is exercising on the exercise machine and performing the activities in the software applications currently executing on the data processing system, and wherein the set of sensors also includes sensors for determining how the user is interacting with the data processing system by monitoring a number of keystrokes per minute and a number of backspacing per minute by the user while performing the activities in the software applications currently executing on the data processing system;
sending, by the data processing system, a signal to a control module of the exercise machine adjusting one or more settings of the exercise machine based on changes in the activities the user is performing in the software applications currently executing on the data processing system at the workstation; and
adjusting, by the data processing system, the one or more settings of the exercise machine based on a current cognitive state of the user determined by a portable brain-wave monitor coupled to the data processing system that monitors the user for measurable cognitive psychophysiological changes indicating the current cognitive state of the user.

14. The computer program product of claim 13 further comprising:
retrieving, by the data processing system, work-related information that includes current job duties corresponding to the user from a storage device.

15. The computer program product of claim 14 further comprising:
adjusting, by the data processing system, the one or more settings of the exercise machine based on the work-related information corresponding to the user.

16. The computer program product of claim 13, wherein the adjusting of the one or more settings of the exercise machine includes at least one of changing a time duration setting, a speed setting, an inclination setting, an interval setting, a resistance setting, and a direction of movement setting.

\* \* \* \* \*